(12) United States Patent  
Sauer et al.

(10) Patent No.: US 6,468,255 B1
(45) Date of Patent: Oct. 22, 2002

(54) FRONT/BACK SEPARATION BARRIER

(75) Inventors: Barbara O. Sauer, Fremont; Melissa C. Putzer, Oshkosh, both of WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 106 days.

(21) Appl. No.: 09/652,541

(22) Filed: Aug. 31, 2000

(51) Int. Cl.$^7$ ................................................. A61F 13/15
(52) U.S. Cl. ........................ 604/385.01; 604/358; 2/267
(58) Field of Search ............................ 2/400–406, 267, 2/268; 604/358–402

(56) References Cited

U.S. PATENT DOCUMENTS

| | | | |
|---|---|---|---|
| 2,625,160 A | * | 1/1953 | Maxim |
| 3,338,992 A | | 8/1967 | Kinney |
| 3,341,394 A | | 9/1967 | Kinney |
| 3,502,763 A | | 3/1970 | Hartmann |
| 3,532,093 A | * | 10/1970 | Lovret |
| 3,542,615 A | | 11/1970 | Dobo et al. |
| 3,603,314 A | * | 9/1971 | Aberg |
| 3,692,618 A | | 9/1972 | Dorschner et al. |
| 3,802,817 A | | 4/1974 | Matsuki et al. |
| 3,849,241 A | | 11/1974 | Butin et al. |
| 4,340,563 A | | 7/1982 | Appel et al. |
| 5,057,368 A | | 10/1991 | Largman et al. |
| 5,069,970 A | | 12/1991 | Largman et al. |
| 5,277,976 A | | 1/1994 | Hogle et al. |
| 5,423,786 A | * | 6/1995 | Fung et al. |
| 5,466,410 A | | 11/1995 | Hills |
| 5,688,259 A | * | 11/1997 | Osborn, III et al. |
| 6,022,338 A | | 2/2000 | Putzer |

FOREIGN PATENT DOCUMENTS

| | | |
|---|---|---|
| WO | 94/14395 | 7/1994 |
| WO | 95/25493 | 9/1995 |
| WO | 96/20674 | 7/1996 |

* cited by examiner

Primary Examiner—Jeanette Chapman
(74) Attorney, Agent, or Firm—Pauley Petersen Kinne & Erickson

(57) ABSTRACT

A personal care absorbent article, such as an infant diaper, a training pant, an incontinence garment and the like, having a structure for forming a separation barrier between a wetting point and a fecal discharge point when the wearer of the personal care absorbent article is in a sitting position. The structure having an expandable region connected to a compressible region whereby the expandable region forms the separation barrier upon compression of the compressible region.

19 Claims, 2 Drawing Sheets

FRONT/BACK SEPARATION BARRIER

BACKGROUND OF THE INVENTION

1. Field of the Invention

This invention relates to personal care absorbent articles, such as disposable diapers, child training pants, adult incontinence garments and the like, having a structure adapted to expand to form a separation barrier when a wearer of the personal care absorbent article is in a sitting position. More particularly, this invention relates to a structure having an expandable region which expands to form the separation barrier when a compressible region connected thereto is compressed.

2. Description of Prior Art

Conventional personal care absorbent articles, such as disposable diapers, child training pants, and incontinence garments employ an absorbent layer positioned between a liquid pervious topsheet and a liquid impervious backsheet to absorb body exudates. These articles typically have elasticized waistbands and legbands to help contain the body exudates and prevent leakage. However, many conventional personal care absorbent articles do not prevent body exudates from migrating through the crotch region of the absorbent article, between the front and the back of the article. Thus, body exudates are free to migrate through the crotch region, resulting in undesired contact with the wearer's skin and leakage.

To help prevent undesirable leakage, some conventional personal care absorbent articles may have compression resistant containment dams which are configured to inhibit the longitudinal flow of fecal material along a surface of the absorbent article contacting the wearer's skin. Such containment dams are positioned within the article so that when the wearer is in a sitting position, the containment dam is positioned along a line where the wearer's buttocks depart from the flat sitting surface. These containment dams may be effective in preventing leakage from a back region of the article but they do not prevent migration of body exudates through the crotch region.

Other conventional personal care absorbent articles may have a partition which extends outwardly from a body facing surface of the absorbent article and provides an abrupt discontinuity between the back portion and the front portion of the absorbent article. Fecal material deposited in the rear portion of the absorbent article is prevented from migrating to the front portion of the absorbent article. However, these partitions are permanently incorporated into the absorbent article and are not responsive to forces exerted by the wearer.

It is apparent that there is a need for a personal care absorbent article which not only isolates and contains body exudates without leakage, but also prevents their migration through the crotch region of the article.

SUMMARY OF THE INVENTION

In response to the discussed difficulties and problems encountered in the prior art, a personal care absorbent article having a structure disposed therein suitable for forming a transverse separation barrier in a gluteal groove when a wearer is in a sitting position, has been discovered.

The personal care absorbent article of this invention comprises an absorbent chassis which defines a front waist region, a back waist region, and a crotch region intermediate to and interconnecting the front waist region and the back waist region. The absorbent chassis also includes a rectangular composite structure having a backsheet, a topsheet which is connected to the backsheet in a superposed relation, and an absorbent layer which is located between the backsheet and the topsheet.

The absorbent chassis includes a structure disposed within the crotch region adapted or suitable for forming a separation barrier. Desirably, the structure is positioned on the topsheet. The structure has an expandable region which transitions into or is connected to a compressible region in such a way that when the compressible region is compressed, the expandable region expands to form the separation barrier.

When the personal care absorbent article is positioned properly on the wearer, the compressible region is adjacent an ischia area of the wearer when the wearer is in a sitting position. In accordance with one embodiment, the compressible region comprises two independent compressible regions separated by the gluteal fold with each compressible region adjacent and contacting one ischium. The expandable region extends transversely across the crotch region of the absorbent chassis and is positioned between a wetting point and a fecal discharge point.

When the wearer is in a sitting position, a force exerted by the ischia area on the compressible region compresses the compressible region and the expandable region expands in a z-direction outwardly from a plane of the article and against the body of the wearer between the wetting point and the fecal discharge point to produce the separation barrier.

Desirably, the separation barrier is made of a pliable material having sufficient expansion force to substantially fill or conform to the body. In an expanded configuration, the separation barrier provides an effective transverse barrier or seal to prevent or obstruct the migration of body exudates longitudinally between the back waist portion and the front waist portion, thereby containing and isolating any body exudates and preventing further undesirable contact with the wearer's skin and/or leakage. Desirably, the separation barrier is a layered structure made of a liquid permeable material to absorb fluids contained within the body exudates.

The structure comprises a material which is resiliently compressible so that the structure returns to its original shape after the compression force is removed. Further, the material must have sufficient strength to withstand the compression force exerted by the ischia area and to obstruct the movement of any body exudates longitudinally through the crotch region.

BRIEF DESCRIPTION OF THE DRAWINGS

These and other objects and features of this invention will be better understood from the following detailed description taken in conjunction with the drawings wherein.

DEFINITIONS

Figure 2:
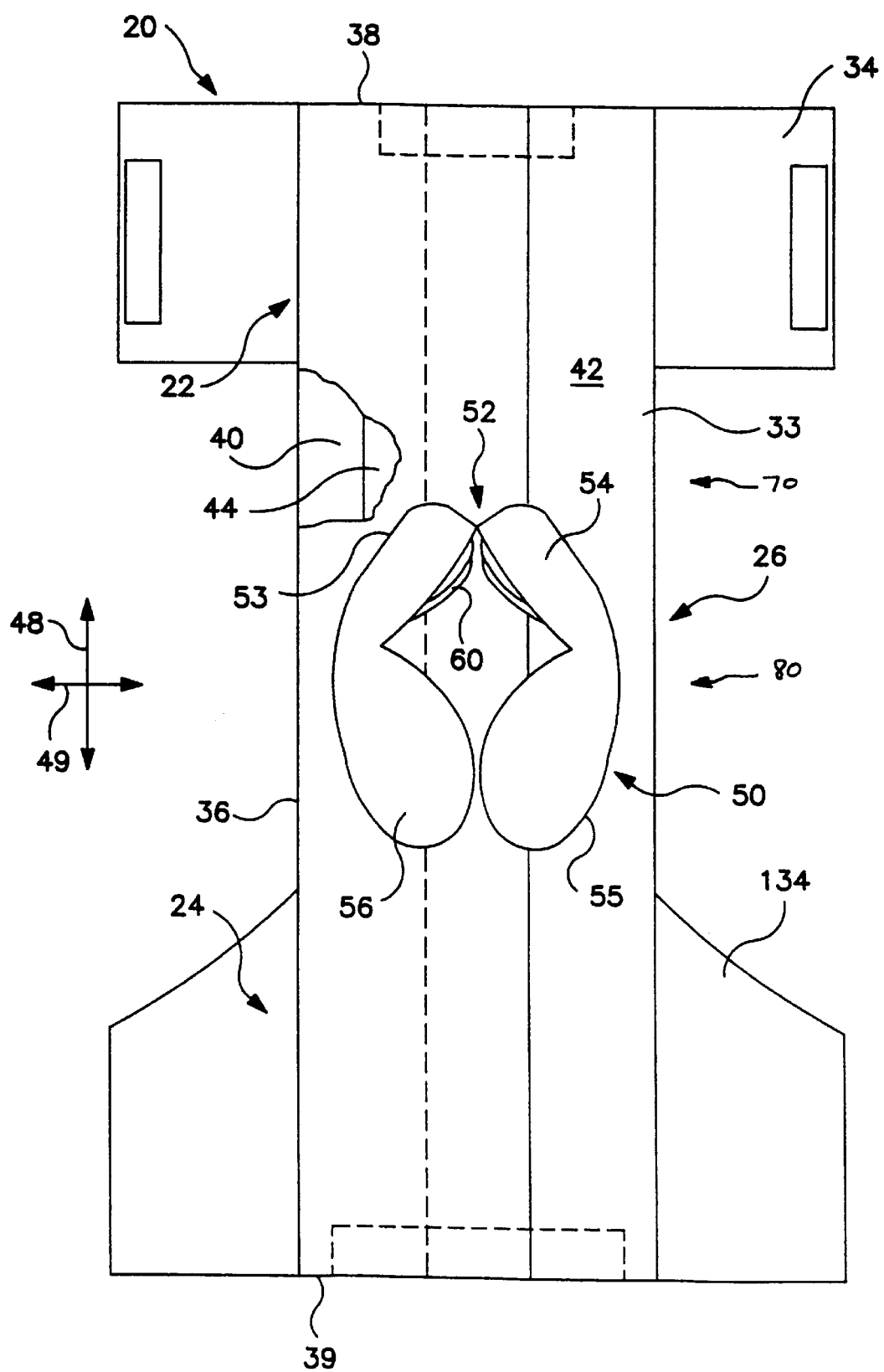
FIG. 2 is a representative plan view of a child's training pant in a flat, uncontracted state, in accordance with one embodiment of this invention.

As used herein, "longitudinal", "transverse" and "lateral" have their customary meaning. The longitudinal axis lies in the plane of the article and is generally parallel to a vertical plane that bisects a standing wearer into left and right body halves when the article is worn. The transverse or lateral axis lies in the plane of the article generally perpendicular to the longitudinal axis. The article as illustrated in FIG. 2 is longer in the longitudinal direction than in the transverse direction. The term "z-direction" refers to a direction not within the plane of the article and desirably, but not necessarily, generally perpendicular to the longitudinal direction and the transverse direction.

As used herein, the term "wetting point" refers to an area of a personal care absorbent article within which urine can be expected to be deposited when the personal care absorbent article is properly positioned on the wearer. The wetting point lies adjacent the urethral orifice of the wearer.

As used herein, the term "fecal discharge point" refers to an area of a personal care absorbent article within which feces can be expected to be deposited when the personal care absorbent article is properly positioned on the wearer. The fecal discharge point lies adjacent the anus of the wearer.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, atactic, syndiotactic and random symmetries.

As used herein, the term "nonwoven" or "nonwoven web" means a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. Nos. 5,069,970 and 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

As used herein, the term "personal care article" or "personal care absorbent article" means feminine hygiene products, diapers, training pants, absorbent underpants, adult incontinence products and wound care products, including bandages.

These terms may be defined with additional language in the remaining portions of the specification.

DETAILED DESCRIPTION OF THE PRESENTLY PREFERRED EMBODIMENTS

The principles of the present invention can be incorporated into any suitable disposable personal care absorbent article. Examples of such suitable articles include disposable infant diapers, training pants, incontinence products, other personal care or health care garments, and the like. For ease of explanation, the description hereafter will be in terms of a child's training pant.

Figure 1:
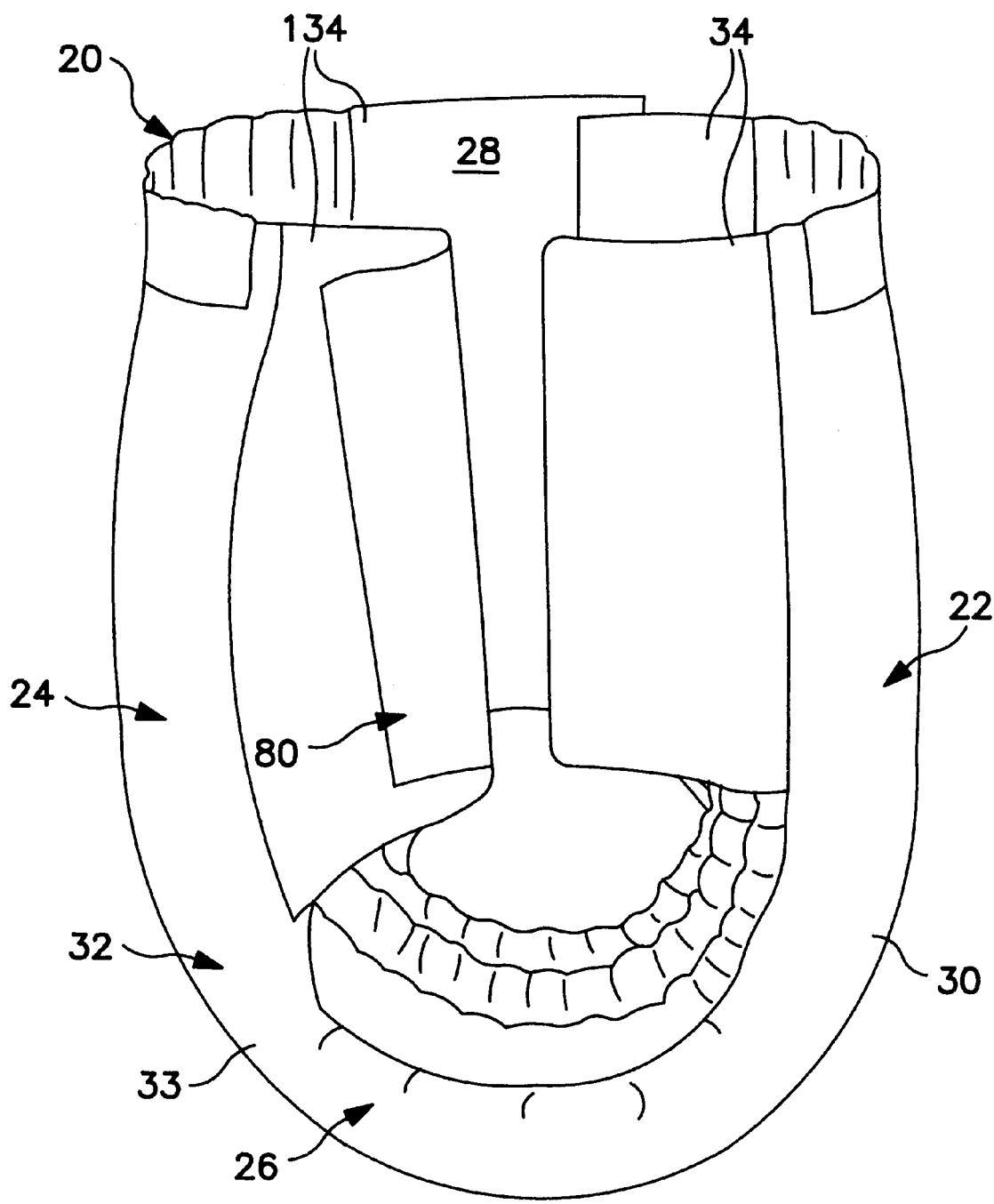
FIG. 1 is a representative perspective view of a child's training pant in a partially fastened position, in accordance with one embodiment of this invention.

As shown in FIG. 1, a disposable absorbent article, such as a training pant 20, comprises an absorbent chassis 32 and a fastening system 80. The absorbent chassis 32 defines a front waist section or region 22, a back waist section or region 24, and a crotch section or region 26 intermediate to and interconnecting the front waist region 22 and the back waist region 24. The front waist region 22 comprises the portion of the training pant 20 which, when worn, is positioned on the front of the wearer while the back waist region 24 comprises the portion of the training pant 20 which, when worn, is positioned on the back of the wearer. The crotch region 26 of the training pant 20 comprises the portion of the training pant 20 which, when worn, is positioned between the legs of the wearer and covers the lower torso of the wearer.

The absorbent chassis 32 further comprises an inner surface 28 which is configured to contact the wearer, and an outer surface 30 opposite the inner surface 28 which is configured to contact the wearer's clothing. As show in FIG. 2, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39, as shown in FIG. 2.

As shown in FIG. 2, the absorbent chassis 32 comprises a rectangular composite structure 33, a pair of transversely opposed front side panels 34, and a pair of transversely opposed back side panels 134. The composite structure 33 comprises a backsheet 40, a topsheet 42 which is connected to the backsheet 40 in a superposed relation, and an absorbent layer 44 which is located between the backsheet 40 and the topsheet 42. For reference, arrow 48 and arrow 49, depicting the orientation of the longitudinal axis and the transverse axis, respectively, of the training pant 20 are illustrated in FIG. 2.

The absorbent chassis 32 is configured to contain and/or absorb any body exudates discharged from the wearer. In accordance with one embodiment of this invention, the absorbent chassis 32 comprises a structure 50 disposed within the crotch region 26 adapted or suitable for forming a separation barrier 52, as shown in FIG. 2. Desirably, the structure 50 is positioned on the topsheet 42, between the topsheet 42 and the wearer. The structure 50 may remain substantially unattached to the topsheet 42 or may be attached to the topsheet 42 using conventional means, such as adhesives. Desirably, the structure 50 is secured to the topsheet 42 in a manner which stabilizes the structure 50 and maintains the structure 50 in a proper position during use. Alternatively, the structure 50 may be disposed within the topsheet 42, the absorbent layer 44 and/or between the topsheet 42 and the absorbent layer 44.

In accordance with one embodiment of this invention, an anterior portion 53 of the structure 50 is angled towards a lateral centerline of the structure 50. The structure 50 desirably has a width which gradually decreases from a posterior portion 55 to the anterior portion 53 to provide a more comfortable fit for the wearer of the training pant 20.

In accordance with one embodiment of this invention, the structure 50 comprises an expandable region 54 which transitions into or is connected to a compressible region 56, as shown in FIG. 2. Desirably, the expandable region 54 is connected with the compressible region 56 in such a way that when the compressible region 56 is compressed, the expandable region 54 expands to form the separation barrier 52.

When the training pant 20 is positioned properly on the wearer, the compressible region 56 is adjacent an ischia area of the wearer, when the wearer is in a sitting position. The term "ischia area" refers to the area corresponding to at least one ischium. The term "ischium" refers to a lower portion of an innominate bone, generally on which the body rests when in a sitting position.

The expandable region 54 extends transversely across the crotch region 26 of the absorbent chassis 32 and is positioned between a wetting point 70 and a fecal discharge point 80. The term "wetting point" refers to the area of the training pant 20 within which urine can be expected to be deposited when the training pant 20 is properly positioned on the wearer. The wetting point lies adjacent the urethral orifice of the wearer. The term "fecal discharge point" refers to the area of the training pant 20 within which feces can be expected to be deposited when the training pant 20 is properly positioned on the wearer. The fecal discharge point lies adjacent the anus of the wearer.

In accordance with one embodiment of this invention, when the wearer is in a sitting position, a pressure or a force exerted by the ischia area on the compressible region 16 compresses the compressible region 56. As a result, the expandable region 54 expands in a z-direction outwardly from a plane of the training pant 20 and against a gluteal groove of the wearer to produce the separation barrier 52 between the wetting point and the fecal discharge point. The term "gluteal groove" generally refers to a continuation of the gluteal fold, of or near the muscles of the buttocks. Desirably, the expandable region 54 expands at a juncture of the gluteal groove and the genitalia of the wearer to produce the separation barrier 52, such that the separation barrier 52 contacts the genitalia but does not obstruct or impede absorption of urine in the front section of the training pant 20.

Desirably, the separation barrier 52 is made of a pliable material having sufficient expansion force to substantially fill or conform to the body's anatomy between the genitalia and the anus. In an expanded configuration, the separation barrier 52 provides an effective barrier or seal to prevent or obstruct the migration of body exudates longitudinally between the back waist portion 24 and the front waist portion 22, thereby containing and isolating any body exudates and preventing further undesirable contact with the wearer's skin and/or leakage. In accordance with one embodiment of this invention, the separation barrier 52 is made of a liquid permeable material to absorb fluids, for example urine. However, in other embodiments, it may be desirable that at least a portion of the structure 50, for example the compressible region 56, be made of a liquid impermeable material in order to achieve greater compressibility and better performance.

The separation barrier 52 expands above the plane of the training pant 20 to an effective height sufficient to prevent longitudinal movement of the body exudates. Desirably, the effective height is about 0.125 inch to about 1.0 inch, more desirably about 0.25 inch to about 0.75 inch. Upon removal of the compression force, for example when the wearer gets up from the sitting position, the compressible region 56 and the expandable region 54 return to their original shape and the separation barrier 52 retracts. In a retracted configuration, the separation barrier 52 has a minimal height and minimal visibility through the training pant 20.

Desirably, the structure 50 is resiliently deformable so that the structure 50 returns to its original shape after the deforming force is removed. Further, the structure 50 must have sufficient strength to withstand the compression force exerted by the ischia area and to prevent the movement of any body exudates longitudinally through the crotch region 26.

Desirably, the separation barrier 52 is capable of resisting z-directional compressive forces which may be exerted by the wearer during use. The compressive forces exerted on the separation barrier 52 are minimized by positioning the separation barrier 52 within the gluteal groove. However, it is desirable that the separation barrier 52 is sufficiently resistant to compression despite the minimal compression forces encountered during use. In one embodiment of this invention, the separation barrier 52 has a z-directional compression resistance of at least about 50 percent, desirably at least about 75 percent, and more desirably at least about 85 percent. The compression resistance of the separation barrier 52 is measured using the Compression Resistance Test discussed below. If the separation barrier 52 has a compression resistance less than these values, the separation barrier 52 may collapse during use which adversely affects the ability of the separation barrier 52 to contain and isolate the body exudates. Conversely, if the compression resistence is too high, the separation barrier 52 may not conform to the gluteal groove and/or may cause undesirable redmarking and irritation to the skin of the wearer.

As discussed above, it is also desirable that the separation barrier 52 be pliable such that it readily conforms to the shape and contours of the wearer's gluteal groove. If the pliability of the separation barrier 52 is too low, the separation barrier 52 may not effectively conform to the body of the wearer and may cause undesired leakage, redmarking and irritation of the skin of the wearer.

Desirablly, the structure 50 comprises a polymer having a high material memory. The term "memory" refers to a material's ability to retain its original configuration upon termination of a deforming force. Suitable polymers include, without limitation, block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Certain elastomeric single-site or metallocene-catalyzed olefin polymers and copolymers are also suitable for the structure 50.

In accordance with one preferred embodiment of this invention, the structure 50 comprises a layered structure for improved absorption and containment of body exudates, as shown in FIG. 2. For example, to provide such improved absorption and containment, the structure 50 may include at least 2 layers, desirably at least about 5 layers, and more desirably at least about 8 layers. The layers are arranged and suitably connected together such that an inner edge 60 of each layer is free to move relative to the adjacent inner edges 60 to readily accept body exudates. Such spacing creates additional surface area on the structure 50 for absorbing exudates, thereby providing improved absorption and containment.

The layers of the structure 50 may be made from any material which provides the desired containment and level of compression resistance. Suitable materials include layers of foams, fibrous webs of natural or synthetic fibers or combinations thereof, and multiple layer fibrous webs. For example, the individual layers of the structure 50 may be crosslinked polyethylene foam material which is commercially available from Sentinel Foams of Hyannis, Mass., under a trade designation EMR NAT. The layers may otherwise include open celled polyester based foam material commercially available from Woodbride Foam Fabricating, Incorporated located in Chattanooga, Tenn., under the trade designation SM-25 BIOFREE ELASTICIZED FOAM. Such foam materials may be particularly desirable because they act like a sponge upon compression and release from the wearer to improve the absorption of exudates.

Alternatively, the layers of the structure 50 may be nonwoven materials such as hydroentangled nonwoven material commercially available from E. I. Dupont de Nemours under the trade designation SON-TARA 8423. Other suitable woven and nonwoven fabrics can be used to construct the structure 50. For example, the structure 50 may include layers composed of a meltblown or spunbond web of polyolefin fibers, or a bonded-carded web or an airlaid web composed of natural and synthetic fibers. The bonded-carded web may, for example, include bicomponent fibers such as bicomponent fibers having a polyethylene sheath and a polyester core. Such woven and nonwoven materials may be treated with a surfactant or otherwise processed to impart a desired level of wettability and hydrophilicity. Similar to the foam materials, the nonwoven materials may also perform like a sponge upon compression and release from the wearer to improve the absorption of exudates.

Further, the layers of the structure 50, desirably the expandable region 54 and the separation barrier 52, may be composed of different materials to provide a compression resistance gradient in the z-direction. For example, the expandable region 54 and the separation barrier 52 may include a nonwoven or soft foam top layer which is highly pliable, allowing the top layer to conform to the gluteal groove. The top layer may also be hydrophobic to repel exudates and maintain a cleaner appearing top surface in contact with the skin of the wearer. The other layers may provide the desired absorption and containment of exudates and the compression resistance to effectively provide stability to the structure 50.

In accordance with one embodiment of this invention, the structure 50 may comprise a partially collapsed enclosure, for example a bladder or a billow. Within the enclosure is a material which is moveable and/or displaceable when pressure is exerted on a portion of the structure 50. For example, when a pressure is exerted on a first portion of the structure 50, the material is displaced from the compressed first portion to a second portion of the structure 50. As a result of the displacement of the material into the second portion of the structure 50, the second portion expands to form the separation barrier 52. Suitable materials include, but are not limited to, a microbead polymer, water and air. Other displaceable materials known to those having ordinary skill in the art may also be used, including solid, semi-solid, liquid and gaseous materials.

The absorbent layer 44 can be any structure which is generally compressible, conformable, non-irritating to the wearer's skin, and capable of absorbing and retaining liquids and certain body exudates, for example SAM/fluff batts, compressed cellulose, foam structures, and the like.

In accordance with one embodiment of this invention, the absorbent layer 44 can be manufactured in a wide variety of sizes and shapes, and from a wide variety of liquid absorbent materials commonly used in the art. For example, the absorbent layer 44 can suitably comprise a matrix of hydrophilic fibers, such as a web of cellulosic fluff, mixed with particles of a high-absorbency material commonly known as superabsorbent material. In a particular embodiment, the absorbent layer 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fiber and natural fibers. The superabsorbent particles can be substantially homogeneously mixed with the hydrophilic fibers or can be nonuniformally mixed. The fluff and superabsorbent particles can also be selectively placed into desired zones of the absorbent layer 44 to better contain and absorb body exudates. The concentration of the superabsorbent particles can also vary through the thickness of the absorbent layer 44. Alternatively, the absorbent layer 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefild, Federal Republic of Germany. Typically, a superabsorbent material is capable of absorbing at least 15 times its weight in water, and desirably is capable of absorbing more than 30 times its weight in water.

In one embodiment, the absorbent layer 44 is generally rectangular in shape, and comprises a blend of wood pulp fluff and superabsorbent material. The absorbent layer 44 may have other suitable shapes. For instance, the absorbent layer 44 may have an angular or tapered configuration to better conform to the wearer's body. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent layer 44 in an amount of from about 5 to about 90 weight percent based on a total weight of the absorbent layer 44. The absorbent layer 44 suitably has a density within the range of about 0.10 to about 0.35 grams per cubic centimeter. The absorbent layer 44 may or may not be wrapped or encompassed by a suitable tissue wrap to maintain the integrity and/or shape of the absorbent layer 44.

The topsheet 42 contacts the skin of the wearer while the training pant 20 is worn and prevents substantial contact of the absorbent layer 44 with the skin of the wearer. The topsheet 42 desirably has soft drape characteristics and good fluid penetration properties while maintaining a dry feel and clothlike aesthetics. The topsheet 42 can be treated to be hydrophilic, to more readily transport body exudates to the absorbent layer 44.

A suitable topsheet 42 can be manufactured from a wide selection of web materials, such as synthetic fibers (for example, polyester or polypropylene fibers), natural fibers (for example, wood or cotton fibers), a combination of natural and synthetic fibers, pirous foams, reticulated foams, apertured plastic films, or the like. Various woven and nonwoven fabrics can be used for the topsheet 42. For example, the topsheet 42 can be composed of a meltblown or spunbond web of polyolefin fibers. The topsheet 42 can also be a bonded-carded web composed of natural and/or synthetic fibers. The topsheet 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire topsheet 42 or can be selectively applied to particular sections of the topsheet 42, such as the medial section along the longitudinal centerline.

A suitable liquid permeable topsheet 42 is a nonwoven bicomponent web having a basis weight of about 1 to about 100 grams per square meter (gsm), suitably about 20 to about 40 gsm, more suitably about 27 gsm. The nonwoven bicomponent web can be a spunbond bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the backsheet 40 and the topsheet 42 can comprise elastomeric materials, it can be desirable in some embodiments for the composite structure to be generally inelastic, where the backsheet 40, the topsheet 42 and the absorbent layer 44 comprise materials that are generally not elastomeric.

The backsheet 40 desirably comprises a material that is substantially liquid impermeable, and can be elastic, stretchable or nonstretchable. The backsheet 40 can be a single layer of liquid impermeable material, but desirably comprises a multi-layered laminate structure in which at least one of the layers is liquid impermeable. For instance, the backsheet 40 can include a liquid permeable outer layer and a liquid impermeable inner layer that are suitably joined together by an laminate adhesive. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which the liquid permeable topsheet 42 is made. While it is not a necessity for the outer layer to be liquid permeable, it is desired that it provides a relatively cloth-like texture to the wearer.

The inner layer and the outer layer can be both liquid and vapor impermeable, or can be liquid impermeable and vapor permeable. The inner layer is desirably manufactured from a thin plastic film, although other flexible liquid impermeable material may also be used. The inner layer, or the liquid impermeable outer cover when a single layer, prevents waste material from wetting articles, such as bedsheets and clothing, as well as the wearer and caregiver. A suitable liquid impermeable film for use as a liquid impermeable inner layer, or a single layer liquid impermeable outer cover, is a 0.02 millimeter polyethylene film commercially available from Huntsman Packaging of Newport News, Va., U.S.A. If the outer cover is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc. Tokyo, Japan, or an XKO-8044 polyolefin film commercially available from 3M Company, Minneapolis, Minn., U.S.A.

Compression Resistance Test

This test is configured to measure the compression resistance of materials intended for use as the separation barrier 52 according to the present invention. The compression resistance of the materials indicates the ability of the material to maintain its shape during use.

A sample of the material intended for use as the separation barrier 52 is obtained. The compression resistance of the material is tested in a standard compressometer such as that commercially available from Frazier Precision Instrument Company, a business having offices located in Gaithersburg, Md. Initially, the compressometer is calibrated. The sample of material is then placed in the compressometer which includes a foot which defines a diameter of 3.0 inches. The foot is positioned in contact with the sample of material and the original height of the material is measured and recorded. The foot is then lowered until the pressure on the material is 1.0 pound per square inch. The compressed height of the material is immediately measured and recorded. The compression resistance value of the material sample is then obtained by dividing the compressed height by the original height and multiplying the result by 100 percent.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention

We claim:

1. A personal care absorbent article comprising:
   a front region, a back region and a crotch region intermediate the front region and the back region; and
   a structure disposed in said crotch region suitable for forming a separation barrier when a wearer of said personal care absorbent article is in a sitting position, wherein said structure comprises an expandable region connected to a compressible region whereby said expandable region expands to form said separation barrier upon compression of said compressible region.

2. A personal care absorbent article in accordance with claim 1, wherein at least a portion of said expandable region extends transversely across the crotch region upon expansion of said expandable region.

3. A personal care absorbent article in accordance with claim 2, wherein the compressible region is compressed by an ischia area when the wearer of the personal care absorbent article is in the sitting position.

4. A personal care absorbent article in accordance with claim 1, wherein the expandable region expands above a surface of the personal care absorbent article.

5. A personal care absorbent article in accordance with claim 1, wherein the separation barrier has an effective height of about 0.125 inch to about 1.0 inch.

6. A personal care absorbent article in accordance with claim 1, wherein the separation barrier has an effective height of about 0.25 inch to about 0.75 inch.

7. A personal care absorbent article in accordance with claim 1, wherein the structure is made of a material selected from the group consisting of a foam, a fiber, a nonwoven web, a laminate and combinations thereof.

8. A personal care absorbent article in accordance with claim 1, wherein the structure comprises a layered structure.

9. A personal care absorbent article in accordance with claim 8, wherein the structure comprises at least two layers.

10. A personal care absorbent article in accordance with claim 1, wherein the separation barrier is made of a liquid permeable material.

11. A personal care absorbent article in accordance with claim 1 comprising a diaper.

12. A personal care absorbent article in accordance with claim 1 comprising training pants.

13. A personal care absorbent article in accordance with claim 1 comprising absorbent underpants.

14. A personal care absorbent article comprising:
    a front region, a back region and a crotch region intermediate the front region and the back region; and
    a structure disposed in said crotch region suitable for forming a separation barrier between a wetting point and a fecal discharge point when a wearer of said personal care absorbent article is in a sitting position, wherein said structure comprises an expandable region connected to a compressible region whereby said expandable region expands to form said separation barrier upon compress ion of said compressible region.

15. A personal care absorbent article in accordance with claim 14, wherein an anterior portion of the structure is angled towards a lateral centerline of the structure.

16. A personal care absorbent article in accordance with claim 14, wherein the structure has a width which gradually decreases from a posterior portion to an anterior portion.

17. A personal care absorbent article in accordance with claim 14, wherein the structure comprises a pliable material.

18. In a personal care absorbent article having a front region, a back region and a crotch region intermediate the front region and the back region, the improvement comprising:
    a structure disposed in said crotch region suitable for forming a separation barrier having a compressible region transitioning into an expandable region, said expandable region expandable to form said separation barrier upon compression of said compressible region.

19. A structure in accordance with claim 18, wherein said expandable region forms said separation barrier which extends transversely across a crotch region of a personal care absorbent article between a wetting point and a fecal discharge point.

* * * * *